United States Patent
Hertel et al.

(10) Patent No.: US 7,412,280 B2
(45) Date of Patent: Aug. 12, 2008

(54) SYSTEMS AND METHODS FOR ANALYZING AN ABNORMALITY OF AN OBJECT

(75) Inventors: Sarah Rose Hertel, Pewaukee, WI (US); Stanley H. Fox, Brookfield, WI (US); Alexander Ganin, Whitefish Bay, WI (US); Charles William Stearns, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 569 days.

(21) Appl. No.: 10/611,296

(22) Filed: Jul. 1, 2003

(65) Prior Publication Data

US 2005/0004452 A1     Jan. 6, 2005

(51) Int. Cl.
*A61B 5/05* (2006.01)
*A61B 6/00* (2006.01)

(52) U.S. Cl. .............. 600/427; 600/407; 600/425; 600/436

(58) Field of Classification Search ............... 600/427
See application file for complete search history.

(56) References Cited

U.S. PATENT DOCUMENTS

| | | | |
|---|---|---|---|
| 4,980,552 | A | 12/1990 | Cho et al. |
| 6,462,342 | B1 | 10/2002 | Stearns |
| 6,490,476 | B1 * | 12/2002 | Townsend et al. ........... 600/427 |
| 6,597,762 | B1 * | 7/2003 | Ferrant et al. ................ 378/62 |
| 6,787,777 | B1 * | 9/2004 | Gagnon et al. ......... 250/363.04 |
| 6,928,142 | B2 * | 8/2005 | Shao et al. .................... 378/63 |
| 7,011,814 | B2 * | 3/2006 | Suddarth et al. ............. 424/9.2 |

* cited by examiner

*Primary Examiner*—Brian L. Casler
*Assistant Examiner*—James Kish
(74) *Attorney, Agent, or Firm*—Dean D. Small; Small Patent Law Group

(57) ABSTRACT

In one embodiment, a method for analyzing at least one abnormality of an object is described. The method includes obtaining a first image containing an abnormality using a first modality, obtaining a second image containing the abnormality using a second modality, selecting a first region of interest located within the first image, determining an anatomical size of the abnormality based on the first region of interest in the first image, and determining a relative metabolic activity based on a second region of interest within the second image.

22 Claims, 6 Drawing Sheets

SYSTEMS AND METHODS FOR ANALYZING AN ABNORMALITY OF AN OBJECT

BACKGROUND OF THE INVENTION

This invention relates to imaging systems and more particularly to systems and methods for analyzing an abnormality of an object.

The systems and methods are directed toward multi-modal medical diagnostic imaging systems capable of scanning using different modalities, such as, for example, but not limited to, Positron Emission Tomography (PET) and Computed Tomography (CT). The term "multi-mode" refers to systems that perform scans in different modes, for example, a flouroscopic mode and a tomosynthesis mode. The term "multi-modal" refers to systems that perform scans in different modalities, for example, CT and PET. It is contemplated that the benefits of systems and methods for analyzing an abnormality of an object accrue to all multi-modal imaging systems, such as, for example, but not limited to, a PET-CT imaging system.

A nodule found during a CT scan often requires a patient many months later to return and obtain another CT scan to determine malignancy based on nodule doubling time. PET scans may be helpful in diagnosis due to increased metabolic activity in the region of the nodule. However, due to the comparatively lower resolution of PET images as compared to CT images, and due to the effects of respiratory or patient motion during a PET scan, nodule activity can be blurred in the PET scan. Consequently, it can be difficult to quantify nodule activity and compare PET. This may result in an indeterminate outcome of the diagnosis of the nodule.

BRIEF DESCRIPTION OF THE INVENTION

In one embodiment, a method for analyzing at least one abnormality of an object is described. The method includes obtaining a first image containing an abnormality using a first modality, obtaining a second image containing the abnormality using a second modality, selecting a first region of interest located within the first image, determining an anatomical size of the abnormality based on the first region of interest in the first image, and determining a relative metabolic activity based on a second region of interest within the second image.

In another aspect, a computer-readable medium encoded with a program is described. The program is configured to instruct a computer to obtain a computed tomography (CT) image containing an abnormality by performing a CT scan of an object, obtain a positron emission tomography (PET) image containing the abnormality by performing a PET scan of the object, select a first region of interest located within the CT image, determine an anatomical size of the abnormality based on the first region of interest in the CT image, and determine a relative metabolic activity based on a second region of interest located on the PET image.

In yet another aspect, a computer is described. The computer is programmed to obtain a CT image containing an abnormality by performing a computed tomography (CT) scan of an object, obtain a PET image containing the abnormality by performing a positron emission tomography (PET) scan of the object, select a first region of interest located within the CT image, determine an anatomical size of the abnormality based on the first region of interest in the CT image, and determine a relative metabolic activity based on a second region of interest located on the PET image.

In still another aspect, an imaging system for analyzing at least one abnormality of an object is described. The imaging system includes a radiation source, a radiation detector, and a controller operationally coupled to the radiation source and the radiation detector. The controller is configured to obtain a first image containing an abnormality by performing a computed tomography (CT) scan of an object, obtain a second image containing the abnormality by performing a positron emission tomography (PET) scan of the object, select a first region of interest located within the first image, determine an anatomical size of the abnormality based on the first region of interest in the CT image, and determine a relative metabolic activity based on a second region of interest located on the second image.

In another aspect, an imaging system for analyzing at least one abnormality of an object is described. The imaging system includes a radiation source, a radiation detector, and a controller operationally coupled to the radiation source and the radiation detector. The controller is configured to obtain a computed tomography (CT) image containing an abnormality by performing a CT scan of an object, obtain a positron emission tomography (PET) image containing the abnormality by performing a PET scan of the object, select a first region of interest located within the CT image, determine an anatomical size of the abnormality based on the first region of interest in the CT image; and determine a relative metabolic activity based on a second region of interest located on the PET image.

DETAILED DESCRIPTION OF THE INVENTION

Figure 1:
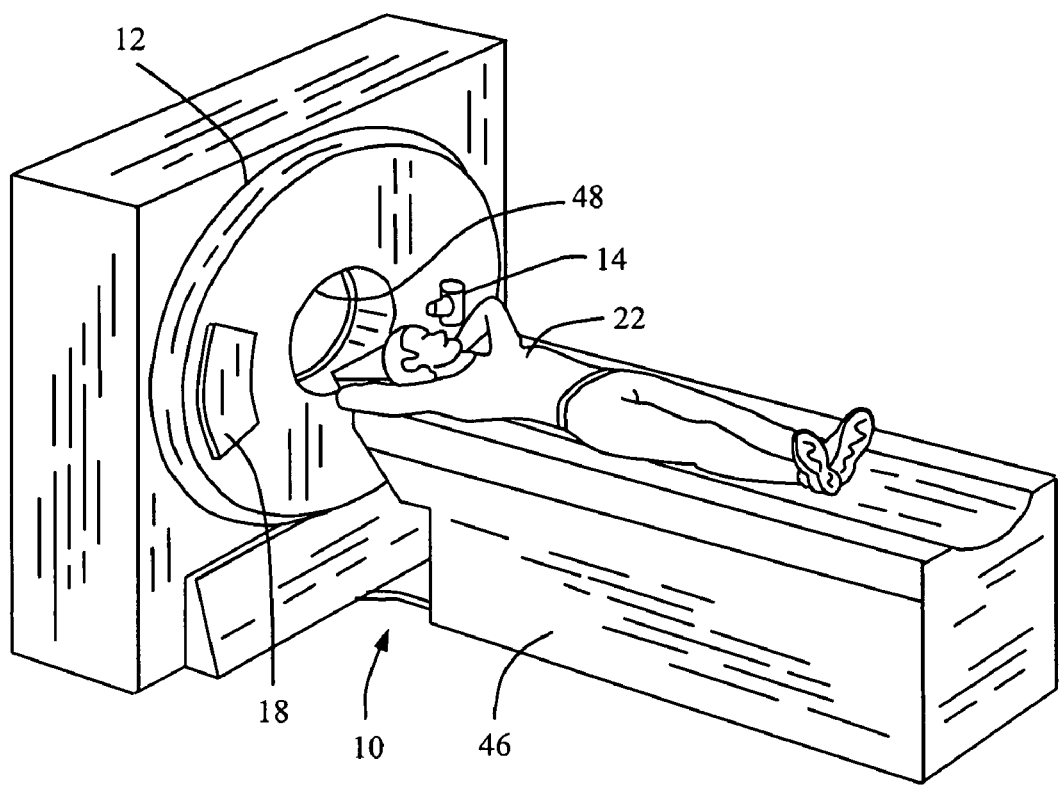
FIG. 1 is a pictorial view of a CT imaging system in which systems and methods for analyzing an abnormality of an object are implemented.

In computed tomography (CT) imaging system configurations, an X-ray source projects a fan-shaped beam which is collimated to lie within an X-Y plane of a Cartesian coordinate system and generally referred to as an "imaging plane". The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements, i.e., projection data, from the detector array at one gantry angle is referred to as a "view". A "scan" of the object comprises a set of views made at different gantry angles, or view angles, during one revolution of the X-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. Positron emission tomography (PET) scanners incorporate a process similar to that found in CT, in that a map or the object attenuation can be generated. A method to perform this attenuation measurement includes use of rotation rod sources containing positron-emitting radionuclides. The rods rotate outside the patient bore, but inside the diameter of the PET detector ring. Annihilation events occurring in the rods can send one photon into a near-side detector while the pair photon traverses the object of interest in a manner similar to the CT X-ray. The data found from this method contains essentially the same information as that found from the CT method except for the statistical quality of the resultant data. In the rotating rod case, the statistical quality is orders of magnitude inferior to most common CT scans. For the PET purpose, data acquired in this manner is used to correct for the attenuation seen in the object by the 511 keV photons, which is often the most substantial correction performed on the PET data.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the object.

At least some CT systems are configured to also perform Positron Emission Tomography (PET) and are referred to as PET-CT systems. Positrons are positively charged electrons (anti-electrons) which are emitted by radio nuclides that have been prepared using a cyclotron or other device. The radionuclides most often employed in diagnostic imaging are fluorine-18 ($^{18}$F), carbon-11 ($^{11}$C), nitrogen-13 ($^{13}$N), and oxygen-15 ($^{15}$O). Radionuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism and protein synthesis. Hereinafter, in the interest of simplifying this explanation, an organ to be imaged including a vessel will be referred to generally as an "organ of interest" and the invention will be described with respect to a hypothetical organ of interest.

After the radiopharmaceutical becomes concentrated within an organ of interest and while the radionuclides decay, the radionuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using PET. First, each gamma ray has an energy of approximately 511 keV upon annihilation. Second, the two gamma rays are directed in nearly opposite directions.

In PET imaging, if the general locations of annihilations can be identified in three dimensions, a three dimensional image of radiopharmaceutical concentration in an organ of interest can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data can be used via any of several different well known image reconstruction methods to reconstruct the three dimensional image of the organ of interest.

As used herein, an element or step recited in the singular and preceded with the word "a" or "an" should be understood as not excluding plural the elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable mages and data representing a viewable image. However, many embodiments generate (or are configured to generate) at least one viewable image.

Figure 2:
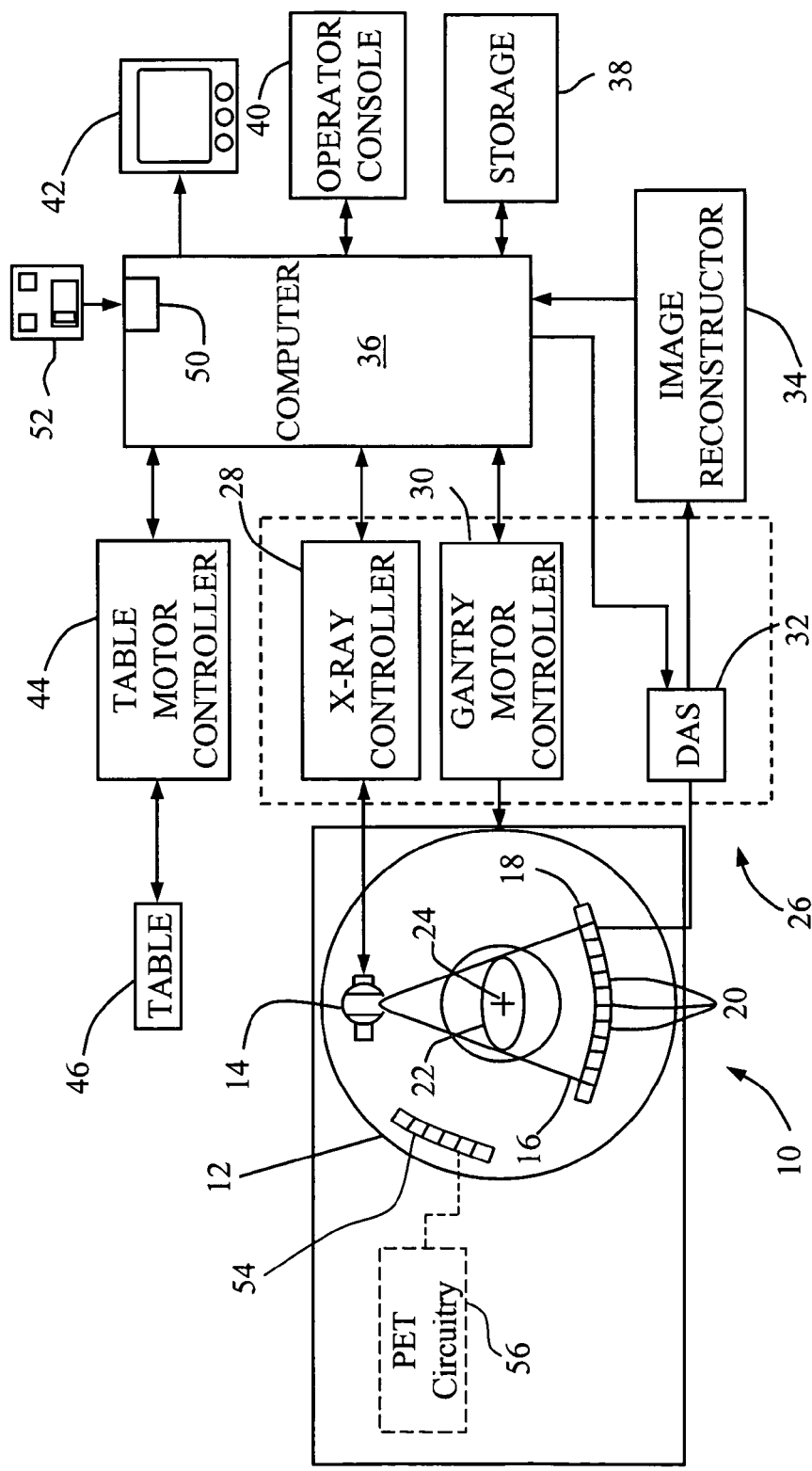
FIG. 2 is a block schematic diagram of the CT imaging system illustrated in FIG. 1.

Referring to FIGS. 1 and 2, a multi-slice scanning imaging system, for example, a CT imaging system 10, is shown as including a gantry 12 representative of a "third generation" CT imaging system. Gantry 12 has an X-ray source 14 that projects a beam of X-rays 16 toward a detector array 18 on the opposite side of gantry 12. Detector array 18 is formed by a plurality of detector rows (not shown) including a plurality of detector elements 20 which together sense the projected X-rays that pass through an object, such as a medical patient 22. Each detector element 20 produces an electrical signal that represents the intensity of an impinging X-ray beam and hence allows estimation of the attenuation of the beam as it passes through object or patient 22. During a scan to acquire X-ray projection data, gantry 12 and the components mounted thereon rotate about a center of rotation 24.

FIG. 2 shows only a detector row of detector elements 20. However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Although the specific embodiment mentioned above refers to a third generation CT system, methods for analyzing an abnormality of an object equally apply to fourth generation CT systems that have a stationary detector and a rotating X-ray source, fifth generation CT systems that have a stationary detector and an X-ray source.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

It is noted that CT imaging system can be combined with a PET imaging system, that is described below, to form a PET-CT imaging system (not shown). In one embodiment, the PET-CT imaging system includes a plurality of PET detectors 54, rotating rod sources (not shown) and a PET circuitry 56 within gantry 12. An example of such as PET-CT system is a Discovery LS PET-CT system commercially available from General Electric Medical Systems, Waukesha, Wis. In another embodiment, the PET-CT imaging system includes the plurality of PET detectors 54 and PET circuitry 56 located with a separate gantry. An example of such a PET-CT system is a Discovery ST system commercially available from General Electric Medical Systems.

Figure 3:
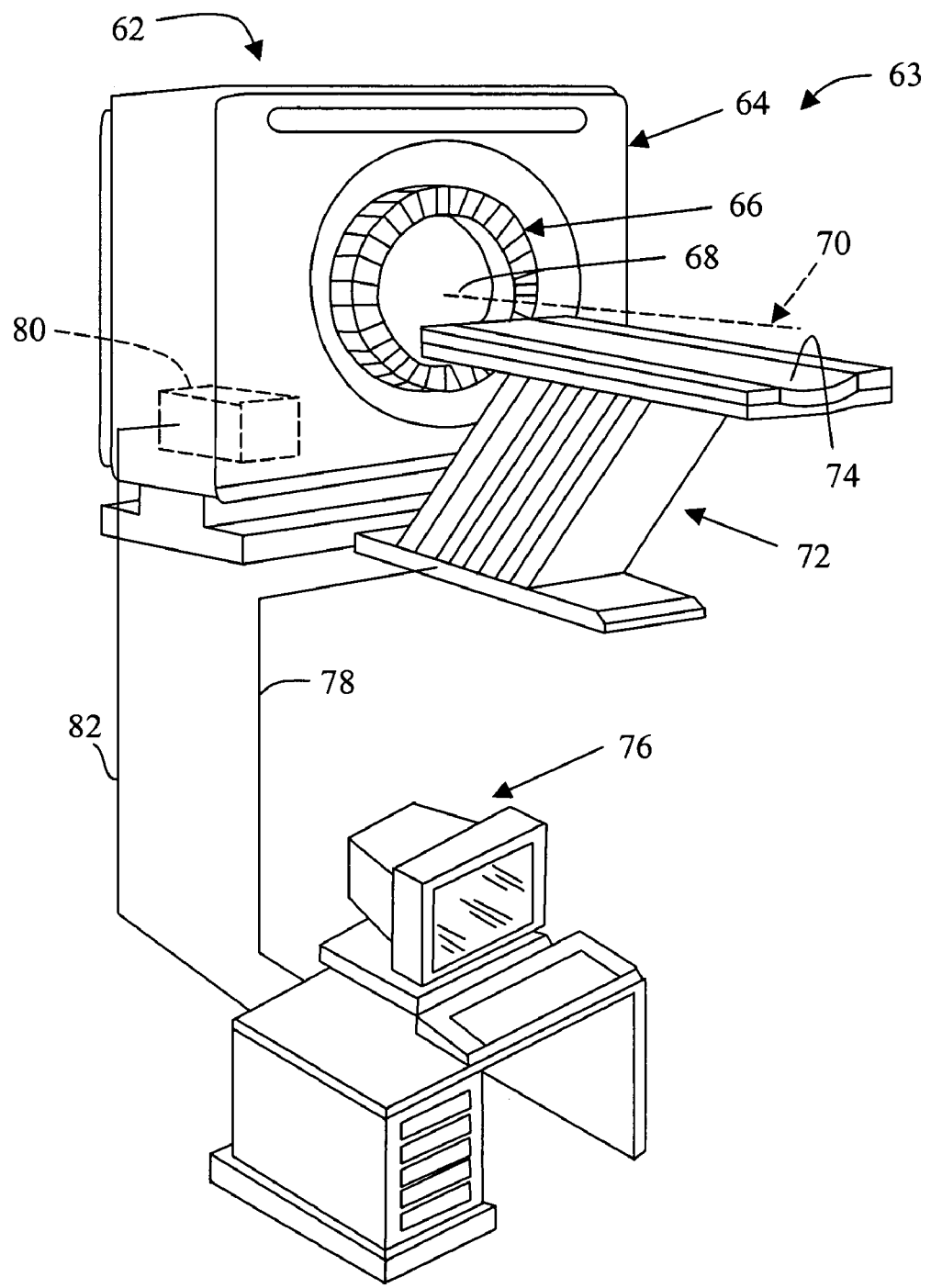
FIG. 3 is an isometric view of an embodiment of a PET imaging system in which systems and methods for analyzing an abnormality of an object are implemented.

FIG. 3 is an isometric view of an embodiment of a PET imaging system 62 in which systems and methods for analyzing an abnormality of an object are implemented. PET imaging system 62 includes a PET scanner 63. PET scanner 63 includes a gantry 64 which supports a detector ring assembly 66 about a central opening, or bore 68. Detector ring assembly 66 is circular in shape, and is made up of multiple detector rings (not shown) that are spaced along a central axis 70 to form a cylindrical detector ring assembly. A table 72 is positioned in front of gantry 66 and is aligned with central axis 70 of detector ring assembly. A table controller (not shown) moves a table bed 74 into bore 68 in response to commands received from an operator work station 76 through a serial communications link 78. A gantry controller 80 is mounted within gantry 64 and is responsive to commands received from operator work station 76 through a second serial communication link 82 to operate gantry 64.

Figure 4:
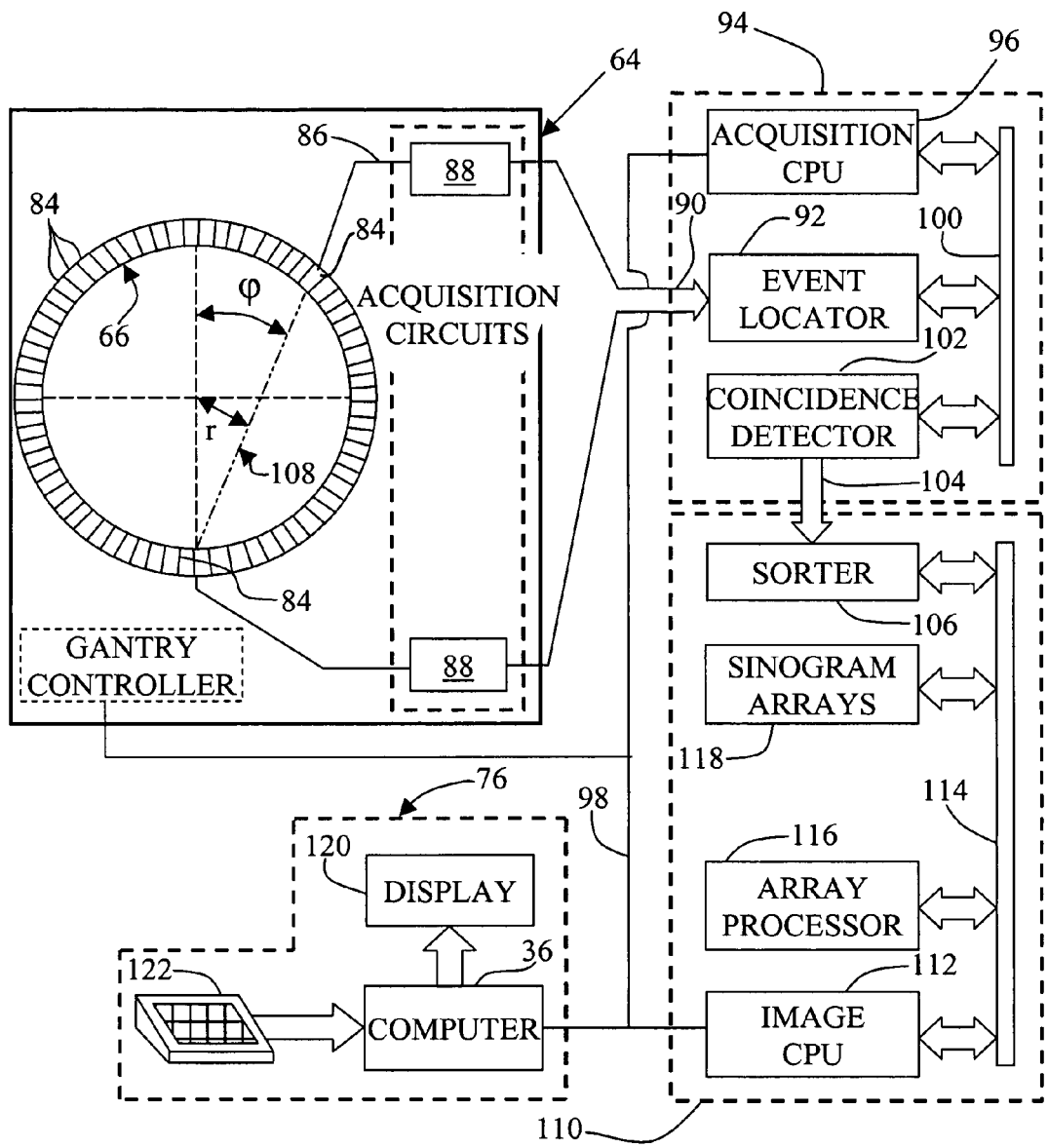
FIG. 4 is a block diagram of the PET imaging system of FIG. 3.

FIG. 4 shows a block diagram of PET imaging system 62 of FIG. 3. Each detector ring of detector ring assembly 66 includes detectors 84. Each detector 84 includes scintillator crystals (not shown). Each scintillator crystal is disposed in front of a photomultiplier tube (PMT) (not shown). PMTs produce analog signals on line 86 when a scintillation event occurs at one of the scintillator crystals that are disposed in front of the PMTs. The scintillation event occurs when a photon is received by one of the scintillator crystals. In one embodiment, photons are generated by administering a compound, such as, $^{11}$C-labeled glucose, $^{18}$F-labeled glucose, $^{13}$N-labeled ammonia and $^{15}$O-labeled water within the object, an emission of positrons by the compounds, a collision of the positrons with free electrons of the object, and generation of simultaneous pairs of photons. Alternatively, the photons are transmitted by rotating rod sources within a FOV of PET imaging system 62. A set of acquisition circuits 88 is mounted within gantry 64 to receive the signals and produce digital signals indicating event coordinates (x,y) and total energy. These are sent through a cable 90 to an event locator circuit 92 housed in a separate cabinet. Each acquisition circuit 88 also produces an event detection pulse (EDP) which indicates the exact moment the scintillation event took place.

Event locator circuits 92 form part of a data acquisition processor 94 which periodically samples the signals produced by acquisition circuits 88. Processor 94 has an acquisition central processing unit (CPU) 96 which controls communications on a local area network 98 and a backplane bus 100. Event locator circuits 92 assemble the information regarding each valid event into a set of digital numbers that indicate precisely when the event took place and the position of a scintillation crystal which detected the event. This event data packet is conveyed to a coincidence detector 102 which is also part of data acquisition processor 94. Coincidence detector 102 accepts the event data packets from event locators 92 and determines if any two of them are in coincidence. Events which cannot be paired are discarded, but coincident event pairs are located and recorded as a coincidence data packet that is conveyed through a serial link 104 to a sorter 106.

Each pair of event data packets that is identified by coincidence detector 102 is described in a projection plane format using four variables r, v, θ, and Φ. Variables r and Φ identify a plane 108 that is parallel to central axis 70, with Φ specifying the angular direction of the plane with respect to a reference plane and r specifying the distance of the central axis from the plane as measured perpendicular to the plane. Variables v and θ (not shown) further identify a particular line within plane 108, with θ specifying the angular direction of the line within the plane, relative to a reference line within the plane, and v specifying the distance of center from the line as measured perpendicular to the line.

Sorter 106 forms part of an image reconstruction processor 110. Sorter 106 counts all events occurring along each projection ray, and stores that information in the projection plane format. Image reconstruction processor 110 also includes an image CPU 112 that controls a backplane bus 114 and links it to local area network 98. An array processor 116 also connects to backplane bus 114. Array processor 116 converts the event information stored by sorter 106 into a two dimensional sinogram array 118. Array processor 116 converts data, such as, for instance, emission data that is obtained by emission of positrons by the compound or transmission data that is obtained by transmission of photons by the rotating rod sources, from the projection plane format into the two-dimensional (2D) sinogram format. Examples of the 2D sinogram include a PET emission sinogram that is produced from emission data and a PET transmission sinogram that is produced from transmission data. Upon conversion of the data into the two-dimensional sinogram format, images can be constructed. Operator work station 76 includes computer 36, a cathode ray tube (CRT) display 120, and a keyboard 122. Computer 36 connects to local area network 98 and scans keyboard 122 for input information. Through keyboard 122 and associated control panel switches, the operator controls calibration of PET imaging system 62, its configuration, and positioning of table 72 for a PET scan. Similarly, once computer 36 receives a PET image and a CT image, the operator controls display of the images on CRT display 120. On receipt of the PET image and the CT image, computer 36 performs a method for analyzing an abnormality of an object.

Figure 5:
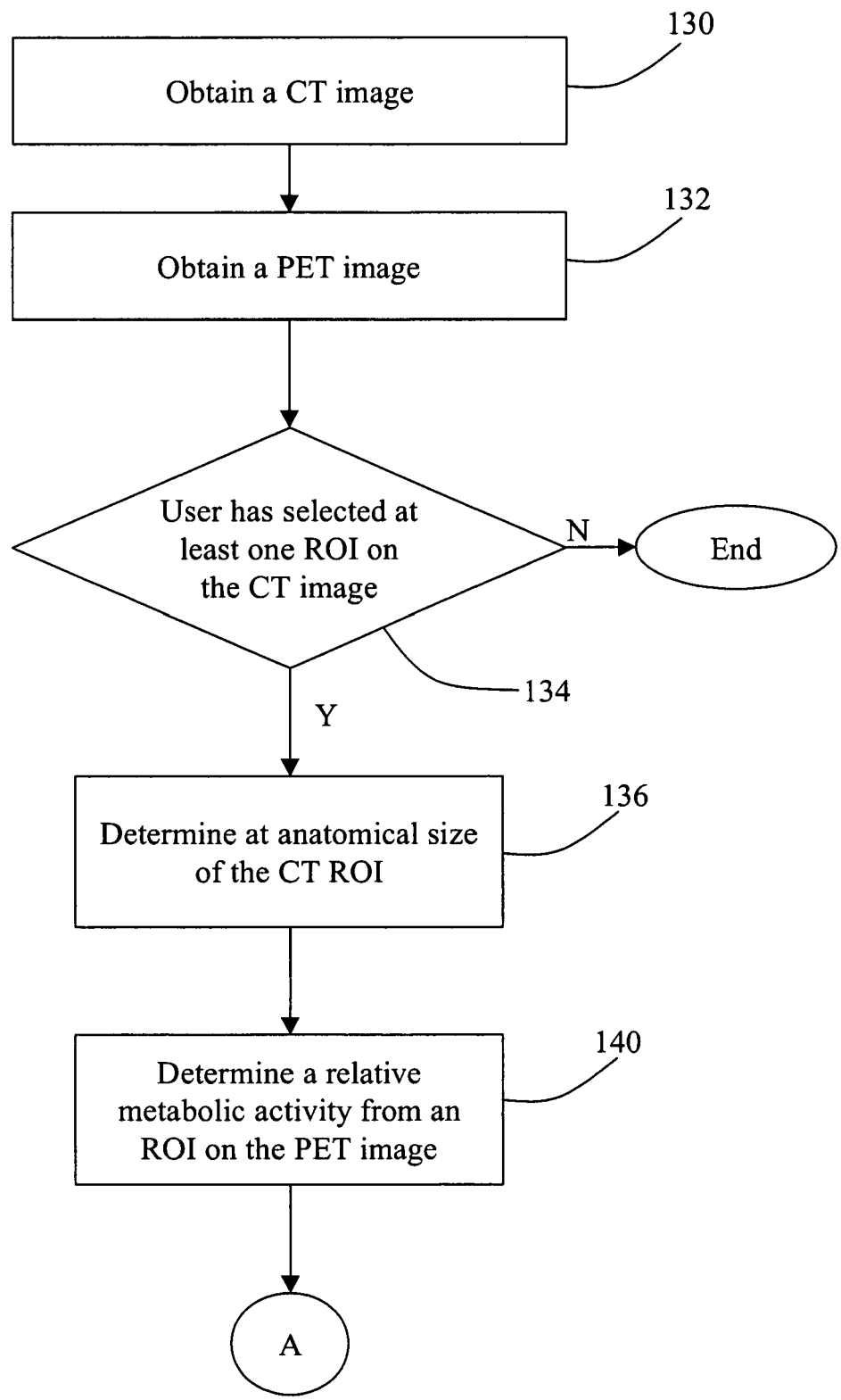
FIGS. 5 and 6 is a flowchart of an embodiment of a method for analyzing an abnormality of an object.
Figure 6:
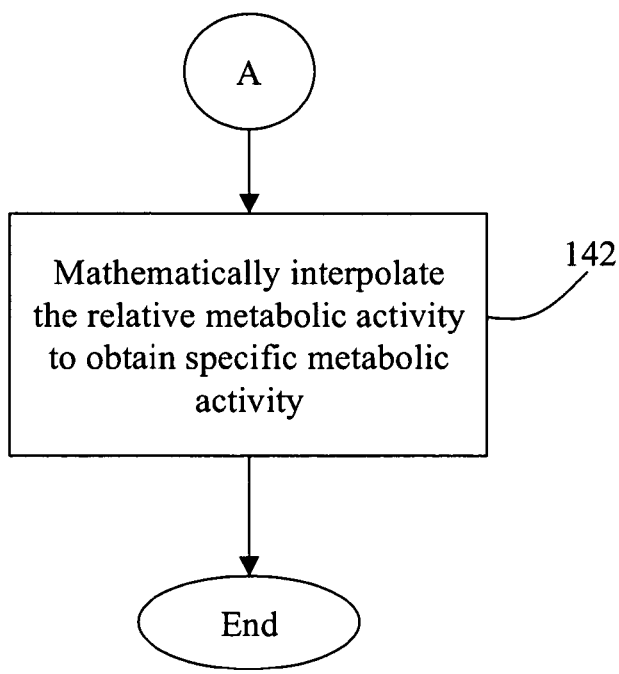
Figure 7:
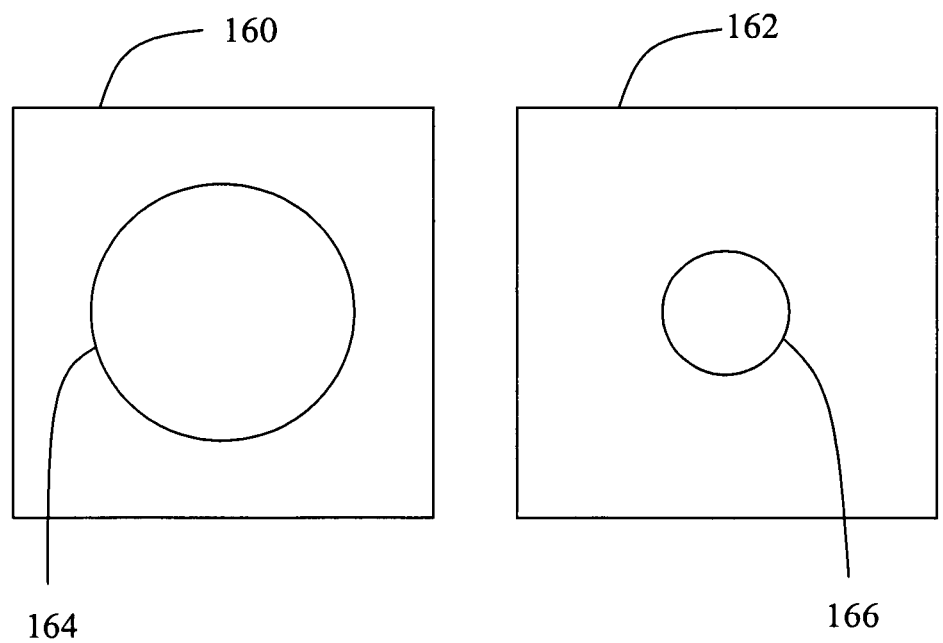
FIG. 7 shows PET and CT images to illustrate the method of FIGS. 5 and 6.

FIGS. 5 and 6 illustrate a flowchart, according to an embodiment of an invention for analyzing an abnormality of an object, such as patient 22, and FIG. 7 shows a CT image 160 and a PET image 162 to illustrate a method for analyzing an abnormality of an object. The method is executed by computer 36. The method is controlled by software and/or is controller by hardware and/or firmware. The method is stored in storage 38 or computer-readable medium 52. In an alternative embodiment, the method can be performed by the PET-CT imaging system that is described above. The method includes obtaining CT image 160 from image reconstructor 34 (step 130). CT image 160 is generated by using CT system 10 to perform a CT scan of an abnormality of patient 22. Examples of abnormalities include an abnormality, such as, a nodule of a lung, of patient 22, an abnormality of a colon of patient 22, an abnormality of a liver of patient 22, an abnormality of a breast of patient 22, an abnormality of an arm of patient 22, and an abnormality of a brain of patient 22. The method further includes obtaining PET image 162 from image CPU 112 (step 132). PET image 162 is produced by using PET system 62 to perform a PET scan of the abnormality within a short period of time after performing the CT scan. An example of the short period of time would be less than 5 minutes.

The method also includes determining (at step 134) whether a user, such as a physician, of PET system 62 and CT system 10 has selected a region of interest (ROI), referred to as CT ROI 164, located on CT image 160. CT ROI 164 corresponds to the abnormality of patient 22. If the user has not selected CT ROI 164, the method ends. Alternatively, if the user has selected CT ROI 164, the method continues by determining (at step 136) an anatomical size of the abnormality from CT ROI 164. An example of the anatomical size of the abnormality includes an area of CT ROI 164. Another example of the anatomical size includes a volume within CT ROI 164. Alternatively, the anatomical size may be determined by executing an Advanced Lung Analysis™ software manufactured by General Electric™ Corporation.

The method further includes determining (at step 140) a relative amount of metabolic activity within an ROI, referred to as PET ROI 166, located on PET image 162. PET ROI 166 corresponds to the abnormality of patient 22. The metabolic activity is relative since CT ROI 164 and PET ROI 166 are of different sizes. For example, in a CT ROI that is of a diameter of 1 centimeter and in a PET ROI that is of a diameter of 2 centimeter, metabolic activity is relative. If CT ROI 164 and PET ROI 166 are of the same size, there is a 1:1 correspondence between the sizes and the metabolic activity is specific.

The method determines the relative metabolic activity from PET ROI 166 by distinguishing metabolic activity within PET ROT 166 from metabolic activity outside PET ROI 166. One example of a technique for calculating and distinguishing metabolic activity is set forth in Lee J R, Madsen M T, Bushnel D, Menda Y, "A threshold method to improve standardized uptake value reproducibility", Nucl Med Commun., 21(7): pp. 685-690, July 2000. The metabolic activity outside PET ROI 166 is referred to as "background activity". Examples of background activity include metabolic activity of tissues located outside the PET ROI, metabolic activity of bones located outside the PET ROI, and metabolic activity of waste material not yet excremented from the bowels. The method distinguishes the metabolic activity within PET ROI 166 from the background activity by determining which voxels within data of PET image 162 has a likilihood, such as, for instance, equal to or greater than 42%, of being related to the abnormality of patient 22. Voxels of PET ROI 166 have the likilihood of being related to the abnormality of patient 22 since a compound such as, for instance, $^{11}$C-labeled glucose, $^{18}$F-labeled glucose, $^{13}$N-labeled ammonia and $^{15}$O-labeled water, is administered into patient 22 and the compound increases the metabolic activity of the abnormality that corresponds to ROI 166.

As shown in FIG. 6, the method further includes mathematically interpolating (in step 142) the relative metabolic activity within PET ROI 166 to determine specific metabolic activity within CT ROI 164. The metabolic activity is specific since the relative metabolic activity is interpolated to determine metabolic activity within CT ROI 164.

Hence, the systems and methods for analyzing an abnormality of an object combines anatomical information obtained from a CT scan and metabolic activity obtained from a PET scan to correct blurred metabolic activity on a PET image. The systems and methods provide information that a physician can share with patient 22 right away instead of waiting months to find the size of the abnormality.

While the invention has been described in terms of various specific embodiments, those skilled in the art will recognize that the invention can be practiced with modification within the spirit and scope of the claims.

What is claimed is:

1. A method for analyzing at least one abnormality of an object, the method comprising:
   obtaining a computed tomography (CT) image containing an abnormality;
   obtaining a positron emission tomography (PET) image containing the abnormality;
   selecting a first region of interest located within the CT image;
   determining an anatomical size of the abnormality based on the first region of interest in the CT image; and determining a relative metabolic activity based on a second region of interest within the PET image; and determining a specific metabolic activity within the first region of interest of the CT image by mathematically interpolating the relative metabolic activity within the second region of interest of the PET image based on the anatomical size of the first region of interest of the CT image, wherein the determined specific metabolic activity is at least one of stored and displayed.

2. A method in accordance with claim 1 wherein obtaining the PET image comprises obtaining the PET image containing the abnormality within a short amount of time after obtaining the CT image.

3. A method in accordance with claim 1 wherein selecting the first region of interest comprises manually selecting the first region of interest located within the CT image.

4. A method in accordance with claim 1 further comprising:
resizing the second region of interest to match the anatomical size determined from the first region of interest.

5. A method in accordance with claim 1 wherein determining a specific metabolic activity comprises determining the specific metabolic activity based at least in part on a difference between the sizes of the first region of interest and the second region of interest.

6. A method in accordance with claim 1 wherein determining the relative metabolic activity comprises distinguishing metabolic activity within the second region of interest from background metabolic activity.

7. A method in accordance with claim 1 wherein determining the relative metabolic activity comprises determining whether the metabolic activity within the second region of interest has a likelihood of being related to the abnormality.

8. A method in accordance with claim 1 wherein determining the anatomical size comprises determining at least one of an area of the first region of interest and a volume of the first region of interest.

9. A method in accordance with claim 1 wherein determining the anatomical size comprises automatically determining a size based on an area of the CT image corresponding to the first region of interest.

10. A computer-readable medium encoded with a program configured to instruct a computer to:
obtain a computed tomography (CT) image containing an abnormality by performing a CT scan of an object;
obtain a positron emission tomography (PET) image containing the abnormality by performing a PET scan of the object;
select a first region of interest located within the CT image;
determine an anatomical size of the abnormality based on the first region of interest in the CT image;
determine a relative metabolic activity based on a second region of interest located on the PET image; and
determine a specific metabolic activity within the first region of interest of the CT image by mathematically interpolating the relative metabolic activity within the second region of interest of the PET image based on the anatomical size of the first region of interest of the CT image, wherein the determined specific metabolic activity is at least one of stored and displayed.

11. A computer-readable medium in accordance with claim 10 wherein to obtain the PET image the program configured to obtain the PET image containing the abnormality using a PET scanner within a short amount of time after obtaining the CT image.

12. A computer-readable medium in accordance with claim 10 wherein to select the first region of interest the program configured to wait for a user to select the first region of interest located within the CT image.

13. A computer-readable medium in accordance with claim 10 wherein to determine the relative metabolic activity the program configured to determine a relative metabolic activity based in part on the anatomical size of the first region of interest.

14. A computer-readable medium in accordance with claim 10 wherein to determine the relative metabolic activity the program configured to distinguish metabolic activity within the second region of interest from background metabolic activity.

15. A computer-readable medium in accordance with claim 10 wherein to determine the relative metabolic activity the program configured to determine whether the metabolic activity within the second region of interest has a likelihood of being related to the abnormality.

16. A computer-readable medium in accordance with claim 10 wherein to determine the anatomical size the program configured to determine at least one of an area of the first region of interest and a volume of the first region of interest.

17. A computer-readable medium in accordance with claim 10 wherein to determine the anatomical size comprises automatically determining a size based on an area of the CT image corresponding to the first region of interest.

18. An imaging system for analyzing at least one abnormality of an object, the imaging system comprising:
a radiation source;
a radiation detector; and
a controller operationally coupled to the radiation source and the radiation detector, the controller configured to:
obtain a first image containing an abnormality by performing a computed tomography (CT) scan of an object;
obtain a second image containing the abnormality by performing a positron emission tomography (PET) scan of the object;
select a first region of interest located within the first image;
determine an anatomical size of the abnormality based on the first region of interest in the first image; and
determine a relative metabolic activity based on a second region of interest located on the second image; and
determine a specific metabolic activity within the first region of interest of the first image by mathematically interpolating the relative metabolic activity within the second region of interest of the second image based on the anatomical size o the first region of interest of the first image, wherein the determined specific metabolic activity is at least one of stored and displayed.

19. An imaging system in accordance with claim 18 wherein to obtain the second image the controller configured to obtain the second image containing the abnormality using a PET scanner within a short amount of time after obtaining the first image.

20. An imaging system in accordance with claim 18 wherein the controller is further configured to mathematically interpolate the relative metabolic activity to determine specific metabolic activity within the first region of interest.

21. An imaging system in accordance with claim 18 wherein to determine the relative metabolic activity the controller configured to determine a relative metabolic activity is based in part on the anatomical size of the first region of interest.

22. An imaging system in accordance with claim 18 wherein the imaging system is a PET-CT system and wherein the abnormality is at least one of a lung nodule, an abnormality of a colon of the object, an abnormality of a liver of the object, an abnormality of a breast of the object, an abnormality of an arm of the object, and an abnormality of a brain of the object.

* * * * *

UNITED STATES PATENT AND TRADEMARK OFFICE
CERTIFICATE OF CORRECTION

PATENT NO. : 7,412,280 B2
APPLICATION NO. : 10/611296
DATED : August 12, 2008
INVENTOR(S) : Sara Rose Hertel et al.

It is certified that error appears in the above-identified patent and that said Letters Patent is hereby corrected as shown below:

Column 9, line 64, Claim 11, please add --is-- between "program" and "configured"

Column 10, lines 2-3, Claim 12, please add --is-- between "program" and "configured"

Column 10, line 8, Claim 13, please add --is-- between "program" and "configured"

Column 10, line 13, Claim 14, please add --is-- between "program" and "configured"

Column 10, line 19, Claim 15, please add --is-- between "program" and "configured"

Column 10, lines 23-24, Claim 16, please add --is-- between "program" and "configured"

Column 10, line 47, Claim 18, please delete "and" after "region of interest in the first image;"

Column 10, line 55, Claim 18, please delete "o" between "size" and "the" and insert --of-- between "size" and "the";

Column 10, line 59, Claim 19, please add --is-- between "controller" and "configured"

Column 11, line 3, Claim 21, please add --is-- between "controller" and "configured"

Claims 11-16 should read as follows:

Column 9: 11. A computer-readable medium in accordance with Claim 10 wherein to obtain the PET image the program is configured to obtain the PET image containing the abnormality using a PET scanner within a short amount of time after obtaining the CT image.

Column 10: 12. A computer-readable medium in accordance with Claim 10 wherein to select the first region of interest the program is configured to wait for a user to select the first region of interest located within the CT image.

Column 10: 13. A computer-readable medium in accordance with Claim 10 wherein to determine the relative metabolic activity the program is configured to determine a relative metabolic activity based in part on the anatomical size of the first region of interest.

UNITED STATES PATENT AND TRADEMARK OFFICE
CERTIFICATE OF CORRECTION

PATENT NO. : 7,412,280 B2
APPLICATION NO. : 10/611296
DATED : August 12, 2008
INVENTOR(S) : Sara Rose Hertel et al.

It is certified that error appears in the above-identified patent and that said Letters Patent is hereby corrected as shown below:

Column 10: 14. A computer-readable medium in accordance with Claim 10 wherein to determine the relative metabolic activity the program is configured to distinguish metabolic activity within the second region of interest from background metabolic activity.

Column 10: 15. A computer-readable medium in accordance with Claim 10 wherein to determine the relative metabolic activity the program is configured to determine whether the metabolic activity within the second region of interest has a likelihood of being related to the abnormality.

Column 10: 16. A computer-readable medium in accordance with Claim 10 wherein to determine the anatomical size the program is configured to determine at least one of an area of the first region of interest and a volume of the first region of interest.

Claims 18, 19 and 21 should read as follows:

Column 10: 18. An imaging system for analyzing at least one abnormality of an object, the imaging system comprising:
a radiation source;
a radiation detector; and
a controller operationally coupled to the radiation source and the radiation detector, the controller configured to:
obtain a first image containing an abnormality by performing a computed tomography (CT) scan of an object;
obtain a second image containing the abnormality by performing a positron emission tomography (PET) scan of the object;
select a first region of interest located within the first image;
determine an anatomical size of the abnormality based on the first region of interest in the first image; and
determine a relative metabolic activity based on a second region of interest located on the second image; and
determine a specific metabolic activity within the first region of interest of the first image by mathematically interpolating the relative metabolic activity within the second region of interest of the second image based on the anatomical size o of the first region of interest of the first image, wherein the determined specific metabolic activity is at least one of stored and displayed.

UNITED STATES PATENT AND TRADEMARK OFFICE
CERTIFICATE OF CORRECTION

PATENT NO.        : 7,412,280 B2
APPLICATION NO. : 10/611296
DATED             : August 12, 2008
INVENTOR(S)       : Sara Rose Hertel et al.

It is certified that error appears in the above-identified patent and that said Letters Patent is hereby corrected as shown below:

Column 10: 19. An imaging system in accordance with Claim 20 wherein to obtain the second image the controller is configured to obtain the second image containing the abnormality using a PET scanner within a short amount of time after obtaining the first image.

Column 11: 21. An imaging system in accordance with Claim 20 wherein to determine the relative metabolic activity the controller is configured to determine a relative metabolic activity is based in part on the anatomical size of the first region of interest.

Signed and Sealed this

Seventh Day of July, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,412,280 B2 | |
| APPLICATION NO. | : 10/611296 | |
| DATED | : August 12, 2008 | |
| INVENTOR(S) | : Sara Rose Hertel et al. | |

It is certified that error appears in the above-identified patent and that said Letters Patent is hereby corrected as shown below:

Column 10, line 47, Claim 18, please delete "and" after "region of interest in the first image;"

Signed and Sealed this
Twenty-eighth Day of December, 2010

David J. Kappos
*Director of the United States Patent and Trademark Office*